United States Patent
McCausland et al.

(10) Patent No.: US 7,357,835 B2
(45) Date of Patent: Apr. 15, 2008

(54) PRODUCTION OF CRYSTALLINE MATERIALS BY USING HIGH INTENSITY ULTRASOUND

(75) Inventors: Linda Jane McCausland, Abingdon (GB); John Patrick Perkins, Ilminster (GB)

(73) Assignee: Accentus PLC, London (GB)

( * ) Notice: Subject to any disclaimer, the term of this patent is extended or adjusted under 35 U.S.C. 154(b) by 235 days.

(21) Appl. No.: 10/514,883

(22) PCT Filed: May 13, 2003

(86) PCT No.: PCT/GB03/02017

§ 371 (c)(1),
(2), (4) Date: Nov. 17, 2004

(87) PCT Pub. No.: WO03/101578

PCT Pub. Date: Dec. 11, 2003

(65) Prior Publication Data

US 2005/0188913 A1    Sep. 1, 2005

(30) Foreign Application Priority Data

May 31, 2002 (GB) ................................. 0212626.6
Feb. 5, 2003 (GB) ................................. 0302555.8

(51) Int. Cl.
*B01D 9/00* (2006.01)
*C30B 1/00* (2006.01)

(52) U.S. Cl. ................. 117/68; 117/2; 117/69; 117/206; 117/207; 23/293 R; 23/295 R; 23/301; 426/238; 600/439; 562/447

(58) Field of Classification Search ............. 117/68, 117/206, 207, 69; 23/295 R, 301, 293 R; 426/238; 600/439; 562/447
See application file for complete search history.

(56) References Cited

U.S. PATENT DOCUMENTS

| | | | | |
|---|---|---|---|---|
| 1,347,350 A | * | 7/1920 | Moore | 117/68 |
| 2,876,083 A | * | 3/1959 | Prietl | 23/295 R |
| 3,892,539 A | * | 7/1975 | Midler, Jr. | 23/301 |
| 4,990,216 A | * | 2/1991 | Fujita et al. | 117/68 |

(Continued)

FOREIGN PATENT DOCUMENTS

| | | |
|---|---|---|
| EP | 0611589 | 8/1994 |
| EP | 1256558 | 11/2002 |

(Continued)

*Primary Examiner*—Yogendra N Gupta
*Assistant Examiner*—Seyed Masoud Malekzadeh
(74) *Attorney, Agent, or Firm*—William H. Holt

(57) ABSTRACT

A crystalline material sufficiently pure for use in pharmaceuticals may be made by forming a saturated solution of the material, changing the temperature of the solution so it becomes supersaturated, and subjecting the solution to irradiation by high intensity ultrasound, the frequency of the ultrasound being scanned over a range of frequencies. For example the ultrasound may be varied between 19.5 and 20.5 kHz, and this variation may be sinusoidal. Preferably the ultrasound is provided only briefly, say for less than 5 s, before allowing the solution to cool gradually without further irradiation. The ultrasound may be applied using a vessel with an array of ultrasonic transducers attached to a wall, so each transducer radiates no more than 3 W/cm² yet the power dissipation within the vessel is between 25 and 150 W/litre. This method can reduce the metastable zone width to less than 10 K. It is applicable in particular to aspartame.

8 Claims, 1 Drawing Sheet

U.S. PATENT DOCUMENTS

Figure 1:
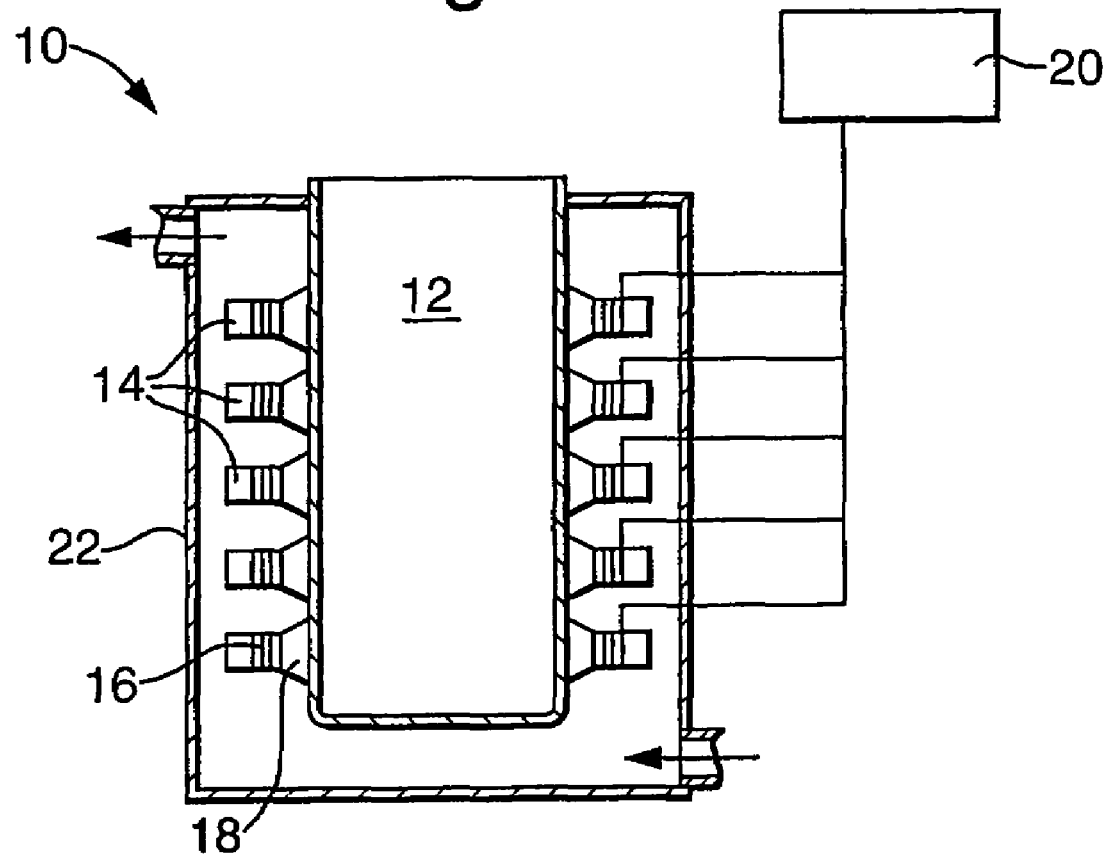

| | | | |
|---|---|---|---|
| 5,830,418 A | 11/1998 | König | 422/245.1 |
| 6,506,250 B1 | 1/2003 | Breitenstein | 117/13 |
| 6,821,339 B2 * | 11/2004 | Eriksson et al. | 117/68 |
| 6,958,040 B2 * | 10/2005 | Oliver et al. | 600/439 |
| 6,966,947 B2 * | 11/2005 | Furuya | 117/68 |
| 6,992,216 B2 * | 1/2006 | Bechtel et al. | 562/447 |
| 2002/0031577 A1 | 3/2002 | Arends | 426/238 |
| 2006/0048699 A1 * | 3/2006 | D'Evelyn et al. | 117/68 |

FOREIGN PATENT DOCUMENTS

| | | |
|---|---|---|
| GB | 2276567 | 10/1994 |
| WO | 96/07461 | 3/1996 |
| WO | 00/33366 | 6/2000 |
| WO | 0035579 | 6/2000 |
| WO | 02/05921 | 1/2002 |
| WO | 02/089942 | 11/2002 |

\* cited by examiner

PRODUCTION OF CRYSTALLINE MATERIALS BY USING HIGH INTENSITY ULTRASOUND

This invention relates to a method for crystallisation of materials that may be suitable for use in pharmaceuticals.

The use of high intensity ultrasound to trigger nucleation in a supersaturated solution, so that crystallisation occurs, is known, and an apparatus for this purpose is for example described in GB 2 276 567 A. The benefits of triggering nucleation in this fashion are of particular relevance when very pure crystalline products are to be formed in a sterile environment, as the purity of the solution and the cleanliness of the vessel surfaces means that crystallisation nuclei are not otherwise present. Certain compounds would be desirable for use in pharmaceuticals, but have been found particularly difficult to crystallise; this relates in particular to disaccharides such as D-glucose or D-xylose. Similar problems arise with other organic compounds such as aspartic acid, and the compound alpha-L-aspartyl-L-phenylalanine methyl ester (aspartame). It has often been found necessary to add crystal modifiers to a saturated solution of such compounds to encourage the formation of crystals, as a saturated solution may have to be cooled considerably below the saturation temperature before crystallisation occurs; with some organic materials this under-cooling may be as much as 100° C. That is to say, a supersaturated solution may remain in a metastable state for a prolonged period, which may be many months. The use of an immersed ultrasonic probe or horn to subject a saturated solution to ultrasound is commonly used, but it has been found that some cavitation occurs at the surface of the horn, this causing slight erosion of the horn and consequential generation of very small metal particles (say about 0.1 mm in diameter); consequently this process would not be acceptable for generating crystalline material for use as a pharmaceutical ingredient.

Accordingly the present invention provides a method for production of crystalline material, the method comprising forming a saturated solution of the material, changing the temperature of the solution so it becomes supersaturated, and subjecting the solution to irradiation by high intensity ultrasound, the frequency of the ultrasound being scanned over a range of frequencies.

For example the ultrasound may be generated by transducers activated to generate signals at a frequency that varies between 19.5 and 20.5 kHz, and the signals from different transducers may vary independently of each other. The frequency may vary sinusoidally (with time) between such limits, or may vary in a sawtooth fashion. The frequency of this modulation may for example lie between 2 and 50 Hz, typically between 5 and 15 Hz. Varying the frequency of the ultrasonic waves has been found to improve the crystallisation process.

Preferably the ultrasound is applied only while the solution is supersaturated, and is applied only until crystals are formed, the crystals in the solution then being allowed to grow without irradiation. Preferably the ultrasound is applied for a time no more than 10 s, for example 2 s or 3 s. The ultrasound most preferably is applied for a brief interval of say less than 5 s, and then the solution inspected to see if any crystals have been formed; if no crystals have been formed than the ultrasound may again be applied for a brief interval, and the solution again inspected. This may be repeated until crystals appear, after which ultrasound is no longer applied. Further gradual cooling of the solution, subsequent to the application of ultrasound, will lead to growth of the crystals formed during the ultrasonic insonation. Hence this method enables large crystals to be grown.

In an alternative approach, such brief bursts of ultrasound may be applied at intervals throughout the cooling of the solution; this is appropriate if the crystals tend to agglomerate, as the brief bursts of ultrasound break up the agglomerations. Alternatively the ultrasound may be applied continuously during cooling; this will tend to cause nucleation and so lead to the formation of very small crystals.

The ultrasound may be applied to the supersaturated solution in a vessel using a multiplicity of ultrasonic transducers attached to a wall of the vessel in an array extending both circumferentially and longitudinally, each transducer being connected to a signal generator so that the transducer radiates no more than 3 W/cm$^2$, the transducers being sufficiently close together and the number of transducers being sufficiently high that the power dissipation within the vessel is between 25 and 150 W/litre. The values of power given here are those of the electrical power delivered to the transducers, as this is relatively easy to determine. Such an irradiation vessel is described in WO 00/35579. Surprisingly it has been found that with such a vessel there is no cavitation at the surface of the wall, so that there is no erosion of the wall and consequently no formation of small particles of metal. The crystalline material made by this method can be very pure, as additives are not required and the crystallisation procedure does not introduce contaminants, so that it would be suitable both for food use and for pharmaceutical use.

It is desirable to ensure no focusing of the ultrasound occurs, and this may be achieved by energising groups of adjacent transducers in succession. Where the vessel is cylindrical it is particularly preferable to avoid energising diametrically opposite transducers at the same time. The non-focusing can also be achieved by energising adjacent transducers, or adjacent groups of transducers, at different frequencies; and in particular varying the frequency at which each transducer or group of transducers is energized over a limited range, for example between 19.5 kHz and 20.5 kHz, thus provides this benefit.

The invention will now be further and more particularly described, by way of example only, and with reference to the accompanying drawing which shows a cross-sectional view of a batch crystallisation irradiator.

Referring to the drawing, a batch crystallisation irradiator 10 includes a stainless-steel vessel 12 of internal diameter 0.31 m and of wall thickness 2 mm. To the outside of the wall are attached sixty transducer modules 14 closely packed in a square array. Each transducer module 14 comprises a 50 W piezoelectric transducer 16 which resonates at 20 kHz, attached to a conically flared titanium coupling block 18 by which it is connected to the wall, the wider end of each block being of diameter 63 mm. The transducer modules define five circumferential rings each of twelve modules 14, the centres of the coupling blocks 18 being on a square pitch of 82 mm. The irradiator 10 also incorporates three signal generators 20 (only one is shown) each of which drives the transducers 16 in a pair of adjacent longitudinal rows and another such pair of rows one third of the circumference apart from the first pair.

In use of the irradiator 10 the vessel 12 is filled with a solution and the temperature of the vessel is gradually lowered (assuming the solubility decreases as the temperature decreases) using a cooling jacket 22, and the contents of the vessel 12 are stirred. Consequently the solution will become saturated and then supersaturated. When the temperature is about 10° C. below that at which saturation occurs, the transducers are energized briefly, each generator 20 being energized for 0.8 s successively. Each transducer irradiates 50 W over a circle of diameter 63 mm, that is an intensity of 1.6 W/cm$^2$. The ultrasonic energy is dissipated over the cylindrical volume of the vessel 12, which is about 31 litres, so if all the transducers 16 were energised simultaneously the power density would be about 100 W/litre. To avoid focusing, only one signal generator 20 is energized at any one time, so the energy deposition is about 33 W/litre. After 0.8 s, a different generator 20 is energized, and so on. After 2.4 s each transducer has been energized, and application of ultrasound is terminated. The contents of the vessel 12 are then inspected, to see if any crystals have formed. If there are no crystals this activation procedure is repeated. Once crystals are observed, application of ultrasound is terminated, and the temperature of the vessel 12 is gradually lowered.

When they are activated, the signal generators 20 generate signals at a frequency that varies between 19.5 and 20.5 kHz, the signals from different signal generators 20 varying independently of each other. The frequency of each signal generator 20 varies sinusoidally with time between those frequency limits, at a frequency of 10 Hz.

With this irradiator 10 the power intensity is such that cavitation does not occur at the surface of the wall, so erosion of the vessel 12 does not occur. Nevertheless the power density is sufficient to ensure nucleation in a saturated solution.

An experiment to investigate the effect of ultrasound on crystallisation has been performed, as follows. An aqueous solution of D-xylose containing 25 g D-xylose per 10 ml water was prepared, which would be saturated at 50° C. This was than cooled at a rate of 0.2 K/min to 20° C., and the resulting solid products were separated and isolated. As a control, in one case the transducers 14 were not energized; in this case crystals did not appear until the temperature had dropped to 36° C. If the transducers 14 were energized for a period of 2 minutes, starting at 46° C., then crystals appeared at 43° C. If the transducers 14 were energized continuously, starting at 50° C., then the resulting crystals were very small, and information on sizes was not obtained. Table 1 gives the temperature T at which solid first appeared and also shows the effect on crystal size distribution by indicating the crystal size (in microns) for different cumulative percentiles (by mass):

TABLE 1

| Conditions | T/° C. | 10% | 50% | 90% |
|---|---|---|---|---|
| no ultrasound | 36 | 27 | 67 | 149 |
| 2 min ultrasound | 43 | 43 | 106 | 211 |
| ultrasound | 46 | — | — | — |

Since the solutions were saturated at 50° C., ideally crystallisation should commence as soon as the temperature drops below 50° C. The short application of ultrasound markedly reduces the metastable zone width to only about 7 K (as compared to about 14 K in the absence of ultrasound). It also gives a significant increase in the crystal sizes that are formed. Continuous application of ultrasound reduces the metastable zone width even more, to about 4 K.

It will be appreciated that the conditions that applied in this particular experiment do not exactly correspond to the method of the present invention, but that the results indicate that it would be appropriate to cool the solution to about 43° C. before subjecting it to brief irradiation.

In performing the present invention, the temperature to which the solution is to be cooled before the brief application of ultrasound will differ for different solutions, depending on the material, the solvent and the concentration, and must therefore be found by experiment. It may be ascertained by experiments similar to those described above. The solution is first subjected to continuous ultrasound as it is cooled, and the temperature at which crystals form (T, which in the example above was 46° C.) is observed. Further tests are then carried out, cooling the solution to different temperatures within a few degrees above or below T to find the highest temperature at which crystals form on application of a brief pulse of ultrasound. Typically this is within 5 K of the temperature T observed with continuous ultrasound.

Aspartame is the alpha-dipeptide ester L-aspartyl-L-phenylalanine methyl ester and is an important synthetic low-calorie sweetening agent. It is about 200 times sweeter than sugar and does not leave a bitter aftertaste, and so is used in a wide range of products. It is however difficult to crystallise without use of crystal modifiers, particularly from aqueous solution. Surprisingly, it has been found possible to produce satisfactory crystals of aspartame directly from an aqueous solution using the present method. A saturated solution of aspartame in warm pure water is prepared, and introduced into the vessel 12. The temperature of the solution is gradually cooled to about 10 K below the temperature at which it would be saturated, and is subjected to ultrasonic irradiation as described above for a short time, for example 2.4 s. The solution is then inspected, and if crystals have formed as a result of the ultrasonic irradiation, then the temperature of the vessel is gradually cooled over a period of a few hours down to room temperature.

This process has been found to produce aspartame crystals between 100 and 250 μm in size, which are easy to separate from the remaining liquid for example by filtration. By avoiding the need for additives the purity of the product is ensured.

The inspection to check if any crystals have formed as a result of the ultrasonic irradiation may be an inspection by eye, while shining a light into the solution, as the small crystals sparkle.

It will be appreciated that the method is applicable using different apparatus, and may be applied on a continuous rather than a batch basis. For example a saturated solution may be caused to flow along a duct in which its temperature gradually decreases, the duct incorporating a flow-through ultrasonic irradiation module at a position at which the solution has reached the appropriate temperature, so that the solution is briefly irradiated as it flows through the module. In this case the transducers of the ultrasonic irradiation module might be activated continuously or in a pulsed mode.

As another application, a saturated solution may be insonated so as to generate crystals, and then be added to a larger volume of solution so that the crystals act as seed crystals for the entire volume. For example there might be 4000 litres of a saturated solution in a crystallisation tank, which is gradually cooled or to which anti-solvent is added. When it is sufficiently supersaturated, a small quantity (eg 40 l) is transferred into an irradiation chamber (eg sucked up through a pipe) at the same temperature as the tank; there it is subjected to ultrasound so that crystals are formed; it is then transferred back into the tank. If no crystals are formed, this operation may be repeated. Hence the entire volume of solution is provided with seed crystals.

The invention claimed is:

1. A method for production of crystalline material, said method comprising the steps of forming a saturated solution of a material, changing the temperature of said solution so that said solution becomes supersaturated, and subjecting said solution to irradiation by high intensity ultrasound, the frequency of said ultrasound being varied over a range of frequencies, said range extending from a predetermined lowest frequency of said range up to a predetermined highest frequency of said range, and said range having a mean frequency and being varied with time in a sinusoidal or sawtooth fashion over said range, for improving crystallization of said material, wherein the difference between the highest and lowest frequency of said range is less than 10% of said mean frequency has been inserted.

2. A method as claimed in claim 1 wherein the frequency of said ultrasound is varied sinusoidally over said range.

3. A method as claimed in claim 1 wherein the ultrasound is generated by a plurality of transducers energised by a plurality of signal generators, and the frequency of the ultrasonic signals from different signal generators are varied in said sinusoidal or sawtooth fashion independently of each other.

4. A method as claimed in claim 1 wherein the ultrasound is applied only while the solution is supersaturated, and is applied only until crystals are formed, the crystals in the solution then being allowed to grow without irradiation.

5. A method as claimed in claim 4 wherein the solution is subjected to ultrasound for less than 10 s.

6. A method as claimed in claim 4 wherein the ultrasound is provided to the supersaturated solution in a vessel using a multiplicity of ultrasonic transducers attached to a wall of the vessel in an array extending both circumferentially and longitudinally, each transducer being connected to a signal generator so that the transducer radiates no more than 3 $W/cm^3$, the transducers being sufficiently close together and the number of transducers being sufficiently high that the power dissipation within the vessel is between 25 and 150 W/litre.

7. A method as claimed in claim 6 wherein groups of adjacent transducers are energised in succession.

8. A method as claimed in claim 6 wherein adjacent transducers, or adjacent groups of transducers, are energised at different mean frequencies.

* * * * *

UNITED STATES PATENT AND TRADEMARK OFFICE
CERTIFICATE OF CORRECTION

| | | |
|---|---|---|
| PATENT NO. | : 7,357,835 B2 | Page 1 of 1 |
| APPLICATION NO. | : 10/514883 | |
| DATED | : April 15, 2008 | |
| INVENTOR(S) | : McCausland et al. | |

It is certified that error appears in the above-identified patent and that said Letters Patent is hereby corrected as shown below:

Column 5, Claim 1, line 14 delete "has been inserted".

Signed and Sealed this
Twenty-fifth Day of December, 2012

David J. Kappos
*Director of the United States Patent and Trademark Office*